(12) United States Patent
Raybin et al.

(10) Patent No.: US 10,349,970 B2
(45) Date of Patent: *Jul. 16, 2019

(54) RESECTION DEVICES AND RELATED METHODS OF DEPLOYMENT

(71) Applicant: Boston Scientific Scimed, Inc., Maple Grove, MN (US)

(72) Inventors: Samuel Raybin, Marlborough, MA (US); Paul Smith, Smithfield, RI (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 199 days.

This patent is subject to a terminal disclaimer.

(21) Appl. No.: 15/264,883

(22) Filed: Sep. 14, 2016

(65) Prior Publication Data

US 2017/0000510 A1    Jan. 5, 2017

Related U.S. Application Data

(63) Continuation of application No. 14/311,021, filed on Jun. 20, 2014, now Pat. No. 9,468,456.
(Continued)

(51) Int. Cl.
*A61B 17/3205* (2006.01)
*A61B 17/221* (2006.01)
(Continued)

(52) U.S. Cl.
CPC .... *A61B 17/32056* (2013.01); *A61B 1/00087* (2013.01); *A61B 1/018* (2013.01);
(Continued)

(58) Field of Classification Search
CPC .......... A61B 17/32056; A61B 1/00087; A61B 1/018; A61B 2017/308;
(Continued)

(56) References Cited

U.S. PATENT DOCUMENTS 5,171,233 A   12/1992   Amplatz et al.
5,417,684 A    5/1995   Jackson et al.
(Continued)

FOREIGN PATENT DOCUMENTS

WO    WO 96/31161 A1    10/1996
WO    WO 02/092148 A2   11/2002

OTHER PUBLICATIONS

International Search Report and Written Opinion for corresponding International Application No. PCT/US2014/043496 dated Nov. 26, 2014, (13 pages).

*Primary Examiner* — Julian W Woo
(74) *Attorney, Agent, or Firm* — Bookoff McAndrews, PLLC

(57) ABSTRACT

A medical/surgical device for performing tissue resection can include an endoscope with proximal and distal ends, defining working channels, and a snare assembly located in one of the working channels. The working channel may include a bend near the distal end and towards the outward radial wall of the endoscope. The snare assembly may include a snare loop and an actuation element imparted with the pre-formed angular bends and an actuation control handle. The bends of the actuation element and the working channel may be the same. The rotational manipulation of the actuation element may synchronize the pre-formed bend of the actuation element with the bend of the working channel to concentrically (or otherwise) align the deployed snare loop with the endoscope or endoscope attachments.

19 Claims, 4 Drawing Sheets

Related U.S. Application Data

(60) Provisional application No. 61/837,795, filed on Jun. 21, 2013.

(51) Int. Cl.
*A61B 1/018* (2006.01)
*A61B 1/00* (2006.01)
*A61B 17/00* (2006.01)
*A61B 17/30* (2006.01)

(52) U.S. Cl.
CPC .. *A61B 17/221* (2013.01); *A61B 2017/00269* (2013.01); *A61B 2017/00331* (2013.01); *A61B 2017/2212* (2013.01); *A61B 2017/2215* (2013.01); *A61B 2017/308* (2013.01)

(58) Field of Classification Search
CPC ........ A61B 2017/00331; A61B 17/221; A61B 2017/00269; A61B 2017/2215
See application file for complete search history.

(56) References Cited

U.S. PATENT DOCUMENTS

| | | | | |
|---|---|---|---|---|
| 5,423,830 | A * | 6/1995 | Schneebaum | A61B 18/10 606/110 |
| 5,643,281 | A * | 7/1997 | Suhocki | A61B 17/32056 606/106 |
| 5,752,961 | A * | 5/1998 | Hill | A61B 17/221 606/110 |
| 5,911,725 | A * | 6/1999 | Boury | A61B 17/22 606/108 |
| 5,976,073 | A * | 11/1999 | Ouchi | A61B 1/00089 600/129 |
| 6,068,603 | A * | 5/2000 | Suzuki | A61B 10/04 600/564 |
| 6,517,550 | B1 * | 2/2003 | Konya | A61B 17/221 606/113 |
| 6,689,051 | B2 * | 2/2004 | Nakada | A61B 1/00089 600/129 |
| 6,699,180 | B2 * | 3/2004 | Kobayashi | A61B 1/00089 600/104 |
| 7,507,200 | B2 * | 3/2009 | Okada | A61B 1/012 600/104 |
| 8,167,893 | B2 * | 5/2012 | Motosugi | A61B 1/0008 600/104 |
| 8,721,663 | B2 * | 5/2014 | Kaplan | A61B 17/1285 606/139 |
| 8,974,470 | B2 | 3/2015 | Lampropoulos et al. | |
| 9,039,713 | B2 * | 5/2015 | Segermark | A61B 17/221 606/113 |
| 9,339,283 | B2 * | 5/2016 | Carroux | A61B 1/307 |
| 9,468,456 | B2 * | 10/2016 | Raybin | A61B 1/00087 |
| 9,539,016 | B2 * | 1/2017 | Lampropoulos | A61B 17/221 |
| 2002/0188262 | A1 * | 12/2002 | Abe | A61B 17/221 604/326 |
| 2005/0209609 | A1 * | 9/2005 | Wallace | A61B 17/221 606/113 |
| 2011/0257477 | A1 | 10/2011 | McWeeney | |
| 2014/0336611 | A1 | 11/2014 | Lizak | |

* cited by examiner

RESECTION DEVICES AND RELATED METHODS OF DEPLOYMENT

CROSS REFERENCE TO RELATED APPLICATIONS

This application is a continuation of U.S. application Ser. No. 14/311,021, filed on Jun. 20, 2014, now U.S. Pat. No. 9,468,456, which claims the benefit of U.S. Provisional Application No. 61/837,795, filed Jun. 21, 2013, each of which is incorporated herein by reference in its entirety.

FIELD OF THE DISCLOSURE

The present disclosure relates generally to resection devices and methods for deployment and, in particular, to a rotating and self-aligning snare configured for deployment for tissue resection.

BACKGROUND

Tissue resection procedures, such as polypectomy, are typically carried out by inserting introduction sheaths, such as endoscopes or laparoscopes, into the body of a patient through incisions or natural anatomical openings. Traditionally, such devices employ snares, typically designed as loops, for performing tissue resection procedures. For scenarios in which the tissue needs to be drawn out before the tissue can be ensnared, such devices may incorporate suction tube(s), employed in tandem with a snare for resection and retrieval of the resected tissue portion(s) from the patient's body.

In some implementations, snares, when deployed, expand into a circular loop, that may not be axially aligned with the operating ends of the endoscopic or laparoscopic attachments, such as suction tubes. Axial misalignment of a deployed snare loop, when used with an endoscopic attachment, sometimes mandates re-deployment of the snare until the snare loop axially aligns with the operating end of the endoscopic attachment, inside the patient's body cavity.

SUMMARY

Embodiments of the present disclosure relate to medical devices for performing tissue-ensnaring procedures during a surgical or medical procedure, e.g., tissue resection from inside a patient's body.

In accordance with an aspect of the present disclosure, a medical device is disclosed for resecting tissue. The device includes an elongate member defined by a proximal end, a distal end, one or more working channels extending from the proximal end to the distal end, and a lumen extending from the proximal end to the distal end, wherein the lumen bends radially outward from the elongate member, near the distal end; and a snare device comprising an actuation element and a snare loop, wherein the snare loop is positioned distal to the distal end of the elongate member and is coupled to an end of the actuation element protruding from the lumen; wherein the actuation element includes a bend at a distal end of the actuation element, wherein the bend in the actuation element interacts with the bend in the lumen to urge the snare loop into alignment with the distal end of the elongate member.

In accordance with another aspect of the disclosure, a snare device is disclosed for deployment through an endoscope and for resection of tissue. The device includes an actuation element configured to be advanced through a lumen extending through the endoscope and bends radially outward from the endoscope near a distal end of the endoscope; and a snare loop coupled to an end of the actuation element and configured to protrude from the lumen and be positioned distal to a distal end of the endoscope; wherein the actuation element is bent at a distal end and the bend in the actuation element is configured to interact with the bend in the lumen to urge the snare loop into alignment with the distal end of the endoscope.

In accordance with another aspect of the disclosure, a method is disclosed for resecting tissue using an elongate member and a snare assembly. The method includes advancing, into a patient orifice, an elongate member defined by a proximal end, a distal end, one or more working channels extending from the proximal end to the distal end, and a lumen extending from the proximal end to the distal end, wherein the lumen bends radially outward from the elongate member, near the distal end; and advancing, through the lumen, a snare device comprising an actuation element and a snare loop, wherein the snare loop is positioned distal to the distal end of the elongate member and is coupled to an end of the actuation element protruding from the lumen; wherein the actuation element includes a bend at a distal end of the actuation element, wherein the bend in the actuation element interacts with the bend in the lumen to urge the snare loop into alignment with the distal end of the elongate member.

Additional characteristics and advantages of the disclosure will be set forth in part in the description, which follows, and in part will be apparent from the description, or may be learned by practice of the disclosure.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain principles of the disclosure.

DESCRIPTION OF EMBODIMENTS

Figure 1:
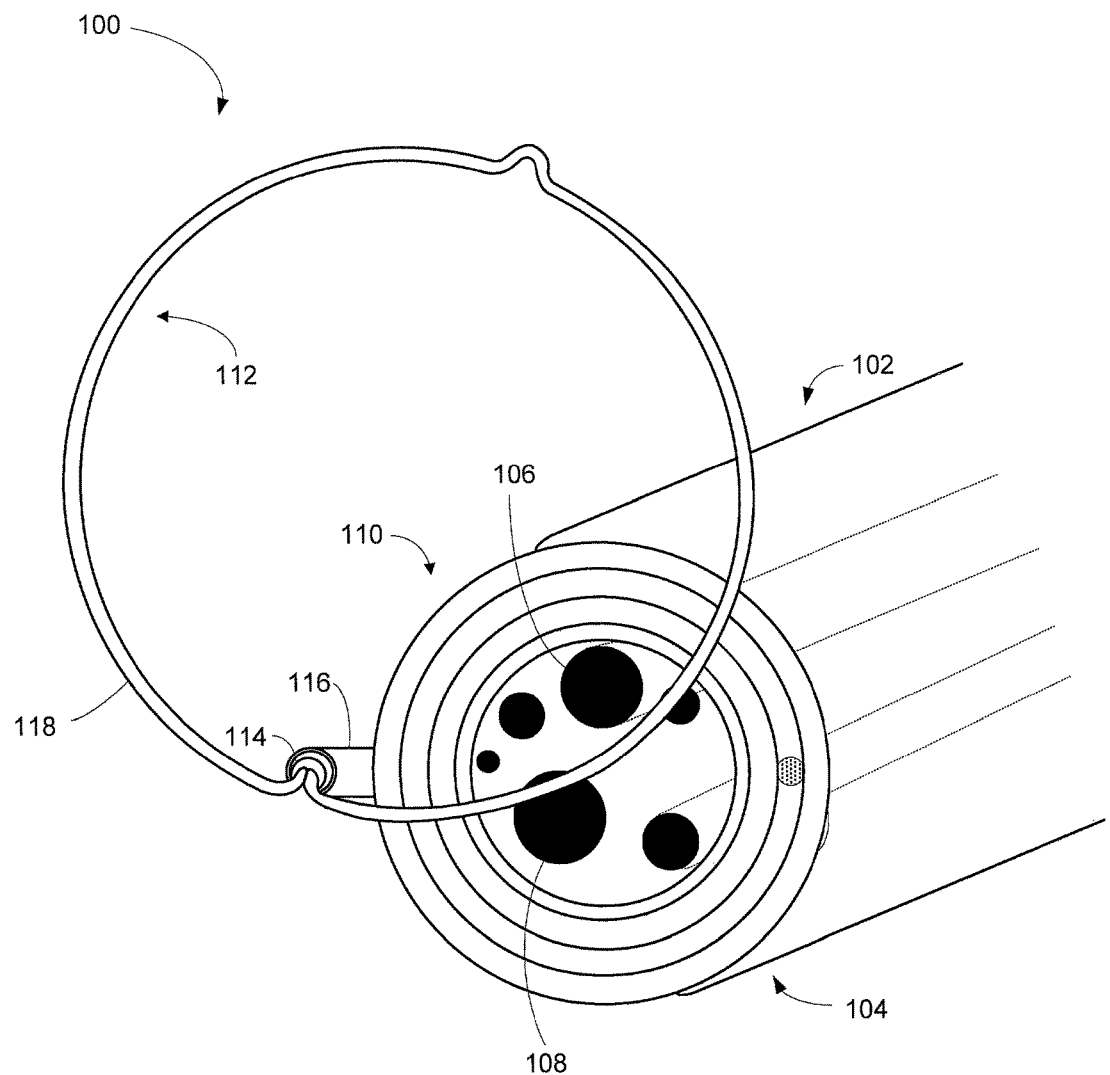
FIG. 1 is a schematic view of a distal portion of a resection device, with an associated snare loop depicted in an expanded configuration, according to certain embodiments of the present disclosure.

Reference is now made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a patient. The term "proximal" refers to the end closest to the user when placing the device into the patient.

Overview

Embodiments of the present disclosure relate to medical or surgical devices used to retrieve and/or sever unwanted or target tissue as well as other unwanted or target material, such as stones, within a patient's body. For example, embodiments of the disclosed device may facilitate removal of unwanted tissue, such as cancerous polyps or lesions, from within a patient's body, including tissue disposed in a patient's body, e.g., on the mucosal walls of the colon, esophagus, stomach, or duodenum. A physician may also desire to resect tissue in order to conduct a biopsy or other examination. For convenience, the medical and surgical devices discussed here can be referred to as "resection devices," it being understood that such devices are equally useful for severing or removing unwanted or target tissue.

In some embodiments, a resection device may include an endoscope, endoscopic attachments (e.g., a suction ring cap), and a snare assembly. The endoscope may include a proximal end, a distal end, and a lumen extended therebetween. The lumen may include multiple working channels. The endoscopic attachments (e.g., the suction ring cap) may be inserted through one of multiple working channels, to be mounted on the distal end of the endoscope and define one or more working channels of the endoscope as a suction channel. The endoscope may incorporate another lumen of having a cylindrical cross-section and being proximal to the radial periphery of the endoscope. The cylindrical cross-sectional lumen may be substantially parallel to the radially outer surface of the endoscope, until the lumen curves radially outward at a distal end. The curvature imparted to the lumen may be toward the radially outer surface of the endoscope, extending the lumen through a slot provided on the radially outer peripheral surface of the endoscope, near the distal end of the endoscope.

The snare assembly may include a snare loop, an actuation element, and an actuation handle. The snare assembly may be introduced at the proximal end of the endoscope and advanced through the cylindrical cross sectional lumen. The actuation element and the snare loop may, in a collapsed configuration, propagate along the length of the curved lumen and emerge near the distal portion of the endoscope through a slot, protruding radially outward.

The actuation element of the snare may also have a pre-formed curvature having an angular bend similar to the curve of the cylindrical cross sectional lumen. The actuation member of the snare assembly may couple to the actuation handle at the proximal end and to the snare loop at the distal end of the endoscope. The snare loop, when deployed at the distal end of the endoscope, may expand to substantial circular shape. In one embodiment, the actuation element may be configured to rotate freely as compelled by forces generated between the curved portion of the lumen and the curved portion of the actuation element. In another embodiment, the actuation handle at the proximal end of the endoscope may be used to rotationally manipulate the actuation element, and seat the pre-formed curvature in the actuation element on the curve in the cylindrical cross-sectional lumen, near the distal portion of the endoscope, to align the expanded snare loop and the suction ring cap in substantially concentric arrangement. The pre-formed curvature of the lumen and the rotational manipulation of the actuation element may allow the deployed snare loop to be offset from the distal opening surface of the suction ring cap, but concentrically aligned with the suction ring cap. The rotation of the actuation element may be controlled by an actuating handle, such as, for example, a guidewire, a resilient mechanism like a spring, or any other suitable mechanism. In various embodiments, the actuation handle may be cylindrical, rectangular, oval, elliptical, conical, and similar configurations.

In various embodiments of the disclosure, the operation of the resection device may be such that the portion of the tissue drawn by the suction channel toward the suction ring cap may be captured, by collapsing the concentrically aligned snare loop around the desired tissue portion, so it may then be resected by the snare. Those skilled in the art will appreciate that the endoscope and the snare assembly may include additional mechanisms and/or other inflatable structures, without departing from the scope of the present disclosure.

Exemplary Embodiments

FIG. 1 is a schematic diagram of an exemplary resection device 100. The resection device 100 may be configured to be introduced into a patient's body through an incision or a suitable natural opening. In addition, the resection device 100 may be configured to be advanced to a desired location within a patient's body with the aid of a suitable introduction sheath, such as an endoscope 102 having a distal end 104, a proximal end (not shown), and one or more working channels 106, 108 extending therebetween.

An operator may introduce one or more medical/surgical devices through one or more working channels 106, 108 of endoscope 102 to extend out of the distal end 104 of the endoscope 102. The operator may also mount an attachment on the distal end 104 of the endoscope 102. For example, during a resectomy procedure, an operator may attach a suction ring cap 110 to the distal end 104 of the endoscope 102, thus rendering one or more channels 106, 108 as a suction channel. Another medical or surgical device, such as a snare assembly 112 may be introduced, for example, into another lumen/channel (not shown). Additionally, from time to time during the procedure, the operator may insert a light source, a camera, an injector, or a morcellator within the one or more channels 106, 108. The proximal end (not shown) of the endoscope 102 may be connected to a hub assembly or handle (not shown) for operating the endoscope 102 and the various devices and attachments inserted into or mounted on endoscope 102, collectively or individually.

The snare assembly 112 may further include a lumen 116, an actuation element 114, an actuation handle (not shown), and a snare loop 118. The actuation element 114 may extend through the entire length of the lumen 116, disposed within a working channel (not shown) of the endoscope 102, and may be manipulated through the actuation handle (not shown), at the proximal end (not shown) of the endoscope 102. Manipulation of the actuation element 114 through the actuation handle may deploy the snare loop 118 at the distal end 104 of the endoscope 102.

The deployed snare loop 118 may expand into a particular shape, such as a substantial circular shape that, in some cases, may not be concentric with the suction ring cap 110. For example, FIG. 1 depicts the snare loop 118 as being out of concentric alignment with the suction ring cap 110, or the distal end 104 of endoscope 102. The axial misalignment of the snare loop 118 may cause various disadvantages, such as in not allowing snare loop 118 to circumferentially grip around targeted tissue, drawn towards the suction ring cap 110 by the suction channel 106, 108. Accordingly, a pre-formed actuation element or feature (described in more detail below) may be incorporated into the snare assembly 112 and/or endoscope 102 to cause the snare loop 118 to align with the operating end of the endoscope 102 during operations, thereby enabling expanded snare loop 118 to effectively ensnare target tissue, drawn toward the suction ring cap 110.

Figure 2:
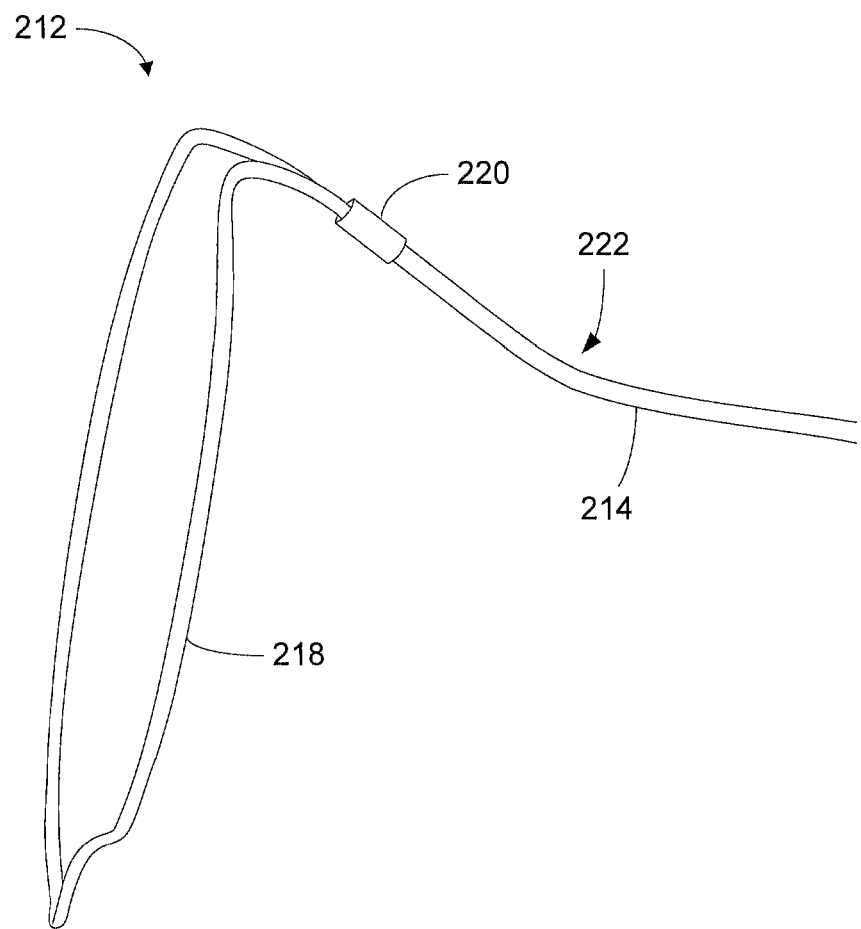
FIG. 2 is a schematic view of an exemplary snare assembly with a snare loop depicted in an expanded configuration, according to certain embodiments of the present disclosure.

FIG. 2 depicts an exemplary snare assembly 212 of a resection device (not shown), in an expanded snare loop configuration, according to principles of the present disclosure. The snare assembly 212 may include an actuation element 214, a snare loop 218, an interface 220 of the actuation element 214 with the snare loop 218, and an actuation handle (not shown). In various embodiments, the actuation element 214 may include, without limitation, a guidewire, a spring mechanism, an actuation tube, a bracket, or a plate with one or more holes and other similar structure(s). The interface 220 may act as a coupling between the actuation element 214 and the snare loop 218. In one example, a push-pull mechanism, such as an actuation wire, may be employed as the actuation element 214 for either manually or automatically expanding and/or retracting the snare loop 218. The manipulation(s) of the actuation element 214 may change the area captured by the snare loop 218 without displacing the snare loop 218 with respect to the targeted tissue.

According to certain aspects of the present disclosure, the actuation element 214 may be angularly curved or imparted with a predetermined obtuse angle, with respect to a longitudinal axis of the actuation element 214, to give it a pre-formed curvature 222. The exact location of the pre-formed curvature 222, along the length of the actuation element 214, may depend upon the structure of a lumen (not shown), through which the actuation element 214 may be inserted in the endoscope (not shown). The actuation element 214 may be fabricated out of any shape memory alloy that can alter the shape of the actuation element 214 through temperature variations or equivalent controlling factors, to impart the pre-formed curvature 222 at the desired location of the actuation element 214. In one embodiment, the pre-formed curvature 222 may be defined by a radius that controls how gently or sharply the actuation element 214 curves. In one embodiment, the pre-formed curvature 222 may be defined by a relatively short radius that causes a relatively sharp or hard angle in the actuation element 214. In another embodiment, the pre-formed curvature 222 may be defined by a relatively long radius that causes a relatively gentle or sloping curve in the actuation element 214.

In one embodiment, the snare loop 218 may be a wire configured to sever or retrieve unwanted tissue. Further, the snare loop 218 may be configured in a variety of shapes, such as a continuous loop, multiple loops, a basket, polygonal loops, non-symmetrical loops, and the like. In one implementation, the snare loop 218 may be substantially circular in shape, however, other configurations may include ellipsoids. In another embodiment, the snare loop 218 may be configured for electrocauterization procedures to resect tissue. For example, the snare loop 218 may be configured to conduct sufficient electric current to generate an amount of heat desired for electrocautery. The snare loop 218 may be substantially hollow with holes disposed on a surface (e.g., an internal surface) to provide irrigation or lubrication during electrocauterization or any other medical or surgical procedure. Furthermore, the snare loop 218 may be configured to withstand repeated heat cycling without developing "hot spots" and breaking down. Further, the general characteristics of suitable materials and configurations of the snare loop 218 known in the art may be used to select adequate materials and configurations for snare loop 218.

In one embodiment, the snare loop 218 may be made of a suitable biocompatible material, e.g., stainless steel or NITINOL. The snare loop 218 may be coated with an antimicrobial covering to inhibit any microbial growth on its surface. For instance, the coating may include an antibacterial covering, which may contain an inorganic antibiotic agent, disposed in a polymeric matrix that adheres the antibiotic agent onto the surface of the snare loop 218. Furthermore, a drug-releasing coating may be applied to the surface of the snare loop 218 for assisting in delivery of drugs to the targeted tissue during operation. The wire of which the snare loop 218 is formed may be sufficiently flexible to retract the snare loop 218 into the collapsed position.

Figure 3:
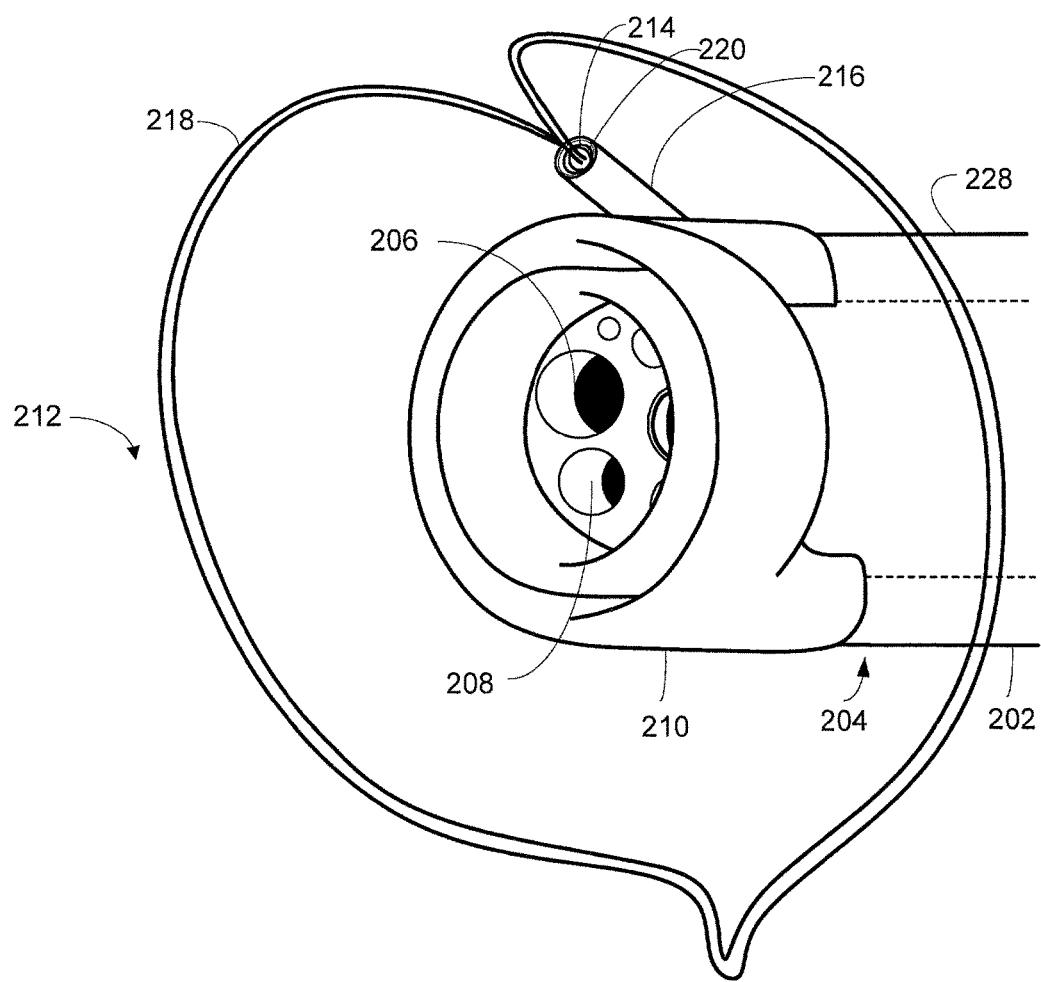
FIG. 3 is a perspective view of an exemplary resection device, incorporating the exemplary snare assembly of FIG. 2, according to certain embodiments of the present disclosure.

FIG. 3 shows a resection device, according to an embodiment of the present disclosure. The resection device may be configured to be introduced into a patient's body through an incision or a suitable natural opening. In addition, the resection device may be configured to be advanced to a desired location within a patient's body with the aid of a suitable introduction sheath, such as an endoscope 202 having a distal end 204, a proximal end (not shown), and one or more working channels 206, 208 extending therebetween. In one embodiment, the resection device may include an endoscope 202 and a snare assembly 212 (as shown in FIG. 2). FIG. 3 depicts snare assembly 212 as being concentrically aligned with distal end 204 of endoscope 202.

Endoscope 202 may include one or more working channels 206, 208 through which an operator may either introduce one or more medical or surgical devices to extend out of the distal end 204 of the endoscope 202. In certain embodiments, an operator may also use an attachment to be mounted on the distal end 204 of the endoscope 202. For example, during a resectomy procedure, an operator may attach a suction ring cap 210 to the distal end 204 of the endoscope 202, thus rendering one or more of channels 206, 208 as a suction channel. Another medical or surgical device, such as a snare assembly 212, may be introduced, for example, into another lumen/channel (not shown). Additionally, from time to time during the procedure, the operator may insert a light source, a camera, an injector, a morcellator, or other device, within the one or more channels. The proximal end (not shown) of the endoscope 202 may be connected to a hub assembly or handle (not shown) for operating the endoscope 202 as well as the various inserted devices and attachments collectively or individually.

In some of the embodiments, one or more of the lumen(s) (not shown) may be disposed in the endoscope 202, proximal to the radially outer periphery of the endoscope 202. The lumen may be of cylindrical cross-section and substantially parallel to the radially outer surface 228 of the endoscope 202, until the lumen is curved radially outward at a distal end of the endoscope 202. The curvature imparted to the lumen may be toward the radially outer surface 228 of the endoscope 202, extending along the lumen to a slot provided (not shown) on the radially outer surface 228 of the endoscope 202, near the distal end 204 of the endoscope 202.

The snare assembly 212 may further include a lumen 216, an actuation element 214, an actuation handle (not shown), and a snare loop 218. In one embodiment, the lumen 216 may be fixedly attached to the endoscope 202 and provided with a permanent curvature at its distal end. Alternatively, the lumen 216 may be introduced from the proximal end (not shown) of the endoscope 202, into the cylindrical cross-sectional lumen (not shown). The lumen 216 may extend along the length of the lumen, substantially parallel and proximal to the radially outer surface 228 of the endoscope 202 until curving radially outward near the distal end 204 of the endoscope 202. The lumen 216 may be a flexible tube that acquires a straight profile when being inserted through endoscope 202, but acquires a curved shape at its distal end, when fully inserted and advanced through endoscope 202. The lumen 216 may emerge from a slot or orifice (not shown) provided at the radially outer surface 228 of the endoscope 202 near the distal end 204 of the endoscope 202. The lumen 216 may be fabricated from silicone, polyurethane, PVC, and/or other such flexible biocompatible polymers and materials.

In some embodiments, the actuation element 214 may be advanced through the entire length of the lumen 216 and can be manipulated through the actuation handle (not shown), at the proximal end (not shown) of the endoscope 202. Manipulation of the actuation element 214 through the actuation handle may deploy the snare loop 218 at the distal end 204 of the endoscope 202. In some embodiments, the actuation element 214 may be imparted with a pre-formed curvature, equivalent to the angle of the curve of the lumen 216. In certain embodiments, the location of the curve along the length of the actuation element 214 may be precisely the same as the curvature of the lumen 216. In one embodiment, the actuation element 214 may be fabricated of shape memory alloy, such as NITINOL, that, by virtue temperature-dependent properties, may allow the actuation element 214 to be imparted with the pre-formed curvature. Thus, actuation element 214 may adopt its pre-formed curvature after being after introduced through the curved lumen 216, along with the collapsed state snare loop 218 and the interface 220. In certain embodiments, the actuation element 214 may acquire its predetermined angular shape or curvature at a location along its length such that the curved portion is aligned with the curved portion of the lumen 216 when the actuation element 214 is fully deployed in the endoscope 202. In one embodiment, the actuation element 214, along with the collapsed state snare loop 218 and interface 220, may be introduced through the proximal end of the endoscope 202 into the curved lumen 216 using any push-pull or similar actuation mechanism, which may be manipulated from the actuation handle (not shown) at the proximal end of the endoscope 202.

Figure 4:
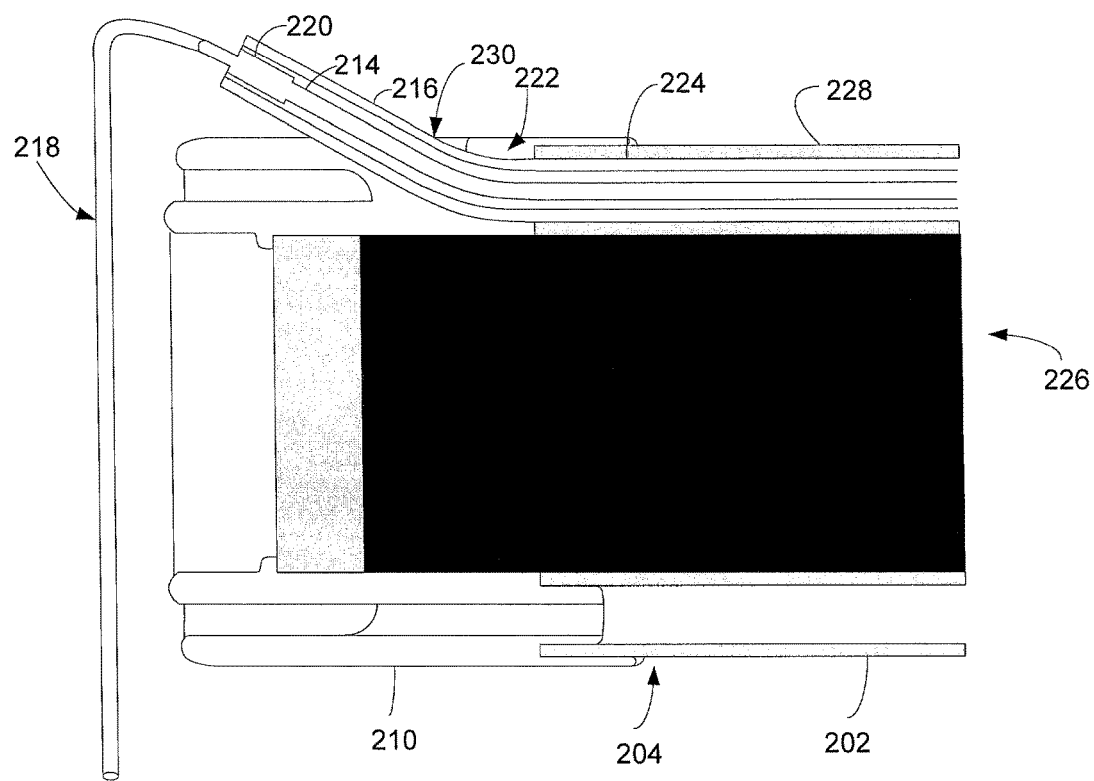
FIG. 4 is a cross-sectional side view of the exemplary resection device of FIG. 3, according to certain embodiments of the present disclosure.

FIG. 4 depicts a cross-sectional side view of a schematic of an exemplary resection device, according to an embodiment of the present disclosure. The resection device may include an endoscope 202, having a proximal end (not shown), a distal end 204, and a lumen 226 extending therebetween. The lumen 226 may further include multiple working channels (206, 208, as shown in FIG. 3), which an operator may use to introduce one or more medical or surgical devices or attachments to be mounted or used at the distal end 204 of the endoscope 202. The medical/surgical devices or attachments may be introduced from the proximal end (not shown) of the endoscope 202, to extend out of the distal end 204 of the endoscope 202.

In some embodiments, apart from the working channels (206, 208, as shown in FIG. 3) available in the lumen 226, additional lumen(s) 224 may be disposed in proximity to the radially outer surface 228 of the endoscope 202. One such lumen 224 of cylindrical cross-section may be disposed in the endoscope 202, between the proximal end (not shown) and slot 230, provided on the radially outer surface 228. Lumen 224 may terminate at or around its distal end at a slot 228 provided on the radially outer surface 228 of the endoscope 202. As described above, lumen 216 may extend through lumen 224 and be imparted with an angular curve at a predetermined location, along its length, proximal to the distal end 204 of the endoscope 202. The imparted curve may be at an obtuse angle with the longitudinal axis of the endoscope 202. The angle and the precise location at which the curvature is introduced in the lumen 216 may depend upon factors, such as, the location of slot 228, and a desired position of snare loop 218.

As described above, during a resectomy procedure, an operator may introduce a snare assembly 212 through the lumen 224, from the proximal end (not shown) of the endoscope 202. The snare assembly 212 may include lumen 216, an actuation element 214, a snare loop 218, an intersection 220 between the actuation element 214 and the snare loop 218, and an actuation handle (not shown). The lumen 216 and the actuation element 214 may each be angularly curved, at locations along their lengths such that they align when the actuation element 214 and its snare loop 218 are fully deployed.

As described above, the curvature 222 may be imparted into actuation element 214 before the snare assembly 212 is introduced in the lumen 224. The actuation handle (not shown) at the proximal end (not shown) of the endoscope 202 can be manipulated to advance the snare assembly 212 along the cylindrical lumen 224. As the actuation element 214, with the pre-formed curvature 222, reaches the curve of the lumen 116, longitudinal force may be applied to the actuation element 214 and or the lumen 216 to cause the snare loop 218 to emerge from the lumen 224, through the slot 230, provisioned on the radially outer surface 228. Moreover, as actuation element 214, with the pre-formed curvature 222, reaches the curve of the lumen 116, respective forces between the actuation element 214 and lumen 116, by virtue of their respective curved portions, may cause actuation element 214 to rotate to a desired orientation that aligns snare loop 218 concentrically with the distal end 204 of endoscope 202.

Specifically, the rotational movement of the actuation element 214 may align the expanded snare loop 218, e.g., concentrically, with an opening in the suction ring cap 210 or generally with a distal end of endoscope 202. In one embodiment, an actuation handle may be used to rotationally manipulate the actuation element 214 for concentric alignment of the snare loop 218, and may be included in the actuation hub (not shown) used for overall deployment of the resection device 200 or individual controls. In another embodiment, the pre-formed curvature 222 of actuation element 214 may act in conjunction with the curve of the lumen 216 to automatically cause the snare loop 218 to become concentric (or otherwise aligned) with the lumen 226 and the distal end 204 of the endoscope 202. In some embodiments, the deployed snare loop 218 may be longitudinally offset from the opening surface of the suction ring cap 210 to provide a better circumferential grip around the targeted tissue.

It should be apparent that the resection device 200 is useful to perform surgical, diagnostic, and therapeutic procedures in a wide variety of bodily locations. For example, removal of polyps detected during a routine colonoscopy could quickly be accomplished using the method discussed above. Additionally, stones or unwanted deposits can be engaged and removed from a variety of body lumens such as ureters, bladders, or the urethra. These and other procedures can be accomplished within the scope of the present disclosure.

Embodiments of the present disclosure may be used in various medical, surgical, or non-medical procedure, including any medical procedure where appropriate resection of undesired or target body tissue is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device for resecting tissue, the device comprising:
    a member including a proximal end, a distal end including a suction cap, at least one working channel extending from the proximal end to the distal end, and a lumen extending from the proximal end to the distal end, wherein the lumen includes a first bend directed radially outward from the member near the distal end; and
    a snare device comprising an actuation element and a snare loop, wherein the snare loop extends distal to the distal end of the member and is at a distal end of the actuation element;
    wherein the actuation element includes a second bend at a distal region of the actuation element, wherein the actuation element includes the second bend prior to insertion of the actuation element into the lumen, wherein the second bend in the actuation element interacts with the first bend in the lumen to urge the snare loop into alignment with the distal end of the member, wherein the lumen remains fixed relative to the member when the second bend in the actuation element interacts with the first bend in the lumen, and wherein the snare loop is configured to be concentrically aligned with the suction cap when the second bend in the actuation element is aligned with the first bend in the lumen.

2. The medical device of claim 1, wherein the lumen extends along a longitudinal axis spaced apart from a central axis of the member, and wherein the first bend in the lumen bends radially away from the central axis of the member near the distal end of the member.

3. The medical device of claim 1, wherein the first bend in the lumen is a single bend, and the second bend in the actuation element is a single bend.

4. The medical device of claim 1, wherein the actuation element is rotatable within the lumen, and relative forces caused by the interaction of the second bend in the actuation element and the first bend in the lumen cause the actuation element to rotate within the lumen.

5. The medical device of claim 1, wherein, prior to insertion of the insertion of the actuation element into the lumen, the second bend in the actuation element and the first bend in the lumen have a common radius of curvature or are bent at a common angle.

6. The medical device of claim 1, wherein the actuation element is curved at a location along its length that causes the snare loop to be longitudinally offset from the distal end of the member when the second bend in the actuation element is aligned with the first bend in the lumen.

7. The medical device of claim 1, wherein at least one of the actuation element and the snare loop is formed from a shape memory material.

8. The medical device of claim 1, wherein the actuation element and the snare loop are configured to be collapsed into a relatively straight configuration when being advanced or retracted through a straight portion of the lumen.

9. The medical device of claim 8, wherein the actuation element is configured to be advanced through the lumen until a position at which the actuation element rotates to align the snare loop, and the second bend in the actuation element attains a curvature matching a curvature of the first bend in the lumen.

10. A medical device for resection of tissue, the device comprising:
    a member including a proximal end, a distal end, at least one working channel extending from the proximal end of the member to the distal end of the member, and a lumen extending from the proximal end of the member to the distal end of the member, wherein the lumen includes a first bend directed radially outward from a longitudinal axis of the member near the distal end of the member; and
    a snare device comprising:
        an actuation element configured to be advanced through the lumen of the member, wherein the actuation element includes a second bend at a distal portion of the actuation element; and
        a snare loop at a distal end of the actuation element and configured to extend distal to the lumen and distal to a distal end of the member;
    wherein the second bend in the actuation element is configured to interact with the first bend in the lumen to urge the snare loop into alignment with the distal end of the member so that the snare loop remains distal to the distal end of the member when the snare loop is in alignment with the distal end of the member, and wherein, when the snare loop is in alignment with the distal end of the member, the first bend in the lumen and the second bend in the actuation element are at a same position relative to the longitudinal axis of the member.

11. The snare device of claim 10, wherein the actuation element is configured to pass through the lumen until the second bend in the actuation element aligns with the first bend in the lumen.

12. The snare device of claim 10, wherein the actuation element is configured to rotate such that relative forces between the second bend in the actuation element and the first bend in the lumen cause the actuation element to rotate.

13. The snare device of claim 10, wherein the second bend in the actuation element and the first bend in the lumen have a common radius of curvature or are bent at a common angle prior to insertion of the actuation element into the lumen.

14. The snare device of claim 10, wherein the actuation element is curved at a location along its length that causes the snare loop to be longitudinally offset from the distal end of the member when the second bend in the actuation element is aligned with the first bend in the lumen.

15. The snare device of claim 10, wherein the actuation element is configured to be advanced through the lumen until a position at which the actuation element rotates to align the snare loop, and the second bend in the actuation element attains a curvature matching a curvature of the first bend in the lumen.

16. A medical device for resecting tissue, the device comprising:
    a member including a proximal end, a distal end, at least one working channel extending from the proximal end to the distal end, and a lumen extending from the proximal end to the distal end, wherein the lumen includes a first bend directed radially outward from the member near the distal end, and wherein a distal opening of the working channel is distal of the first bend in the lumen; and a snare device comprising an actuation element and a snare loop, wherein the snare loop extends distal to the distal end of the member and is at a distal end of the actuation element;

wherein the actuation element includes a pre-formed second bend at a distal region of the actuation element, and wherein the second bend in the actuation element has the same angle of curvature as the first bend and is positioned at the first bend in the lumen to urge the snare loop into concentric alignment with the distal end of the member.

17. The medical device of claim 16, wherein the lumen extends along a longitudinal axis spaced apart from a central axis of the member, and wherein the first bend in the lumen bends radially away from the central axis of the member near the distal end of the member.

18. The medical device of claim 16, wherein the snare loop remains distal to the distal end of the member when the snare loop is in alignment with the distal end of the member.

19. The medical device of claim 16, wherein the distal end of the member includes a suction cap, and the snare loop is configured to be concentrically aligned with the suction cap when the second bend in the actuation element is aligned with the first bend in the lumen.

* * * * *